(12) United States Patent
Koveal et al.

(10) Patent No.: US 6,559,191 B1
(45) Date of Patent: May 6, 2003

(54) CARBON MONOXIDE HYDROGENATION (JSS-0004)

(75) Inventors: Russell John Koveal, Baton Rouge; Michel A. Daage, Baton, both of LA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 185 days.

(21) Appl. No.: 09/653,718

(22) Filed: Sep. 1, 2000

(51) Int. Cl.$^7$ .......................... C07C 27/00; B01J 20/34; B01J 23/00; B01J 23/40
(52) U.S. Cl. ................. 518/709; 518/700; 518/713; 518/715; 502/20; 502/325; 502/326
(58) Field of Search ................ 518/700, 715, 518/713, 709; 502/20, 325, 326

(56) References Cited

U.S. PATENT DOCUMENTS

| | | | | |
|---|---|---|---|---|
| 4,826,799 A | * | 5/1989 | Cheng et al. ................ | 502/301 |
| 4,895,994 A | * | 1/1990 | Cheng et al. ................ | 585/270 |
| 5,536,694 A | * | 7/1996 | Schuetz et al. ............. | 502/301 |

\* cited by examiner

Primary Examiner—Johann Richter
Assistant Examiner—J. Parsa
(74) Attorney, Agent, or Firm—Jay Simon

(57) ABSTRACT

A method is disclosed for enhancing the activity of a particulate Dispersed Active Metal (DAM) catalyst during operation of a reactor wherein the hydrogenation of carbon monoxide to produce a mixture of hydrocarbons is being carried out comprising withdrawing a mixture of hydrocarbons and a portion of the DAM catalyst from the reactor, reducing the hydrocarbon content thereof with hydrogen at a temperature above the temperature of the reactor, oxidizing a slurry of the catalyst particles in a suitable fluid at low temperature to form an oxidized precursor, reducing the precursor at elevated temperature to reform the catalyst and returning it to the reactor. The catalyst may be passivated before returning to the reactor. The process is carried out until it is evident that the operation of the reactor will no longer be economical due to a decrease in catalyst performance or accumulation of fines at which point the catalyst is preferably renewed during operation of the reactor by a process comprising withdrawing a mixture of hydrocarbons and a portion of the DAM catalyst, reducing the hydrocarbon content thereof, heating the mixture above the melting temperature of at least one of the metals to form a melt, removing any slag that forms on the melt, cooling the melt to form a solid, reducing the particle size thereof to form a renewed particulate DAM catalyst, which is then returned to the reactor.

19 Claims, No Drawings

CARBON MONOXIDE HYDROGENATION
(JSS-0004)

This invention relates to the production of higher hydrocarbons from synthesis gas utilizing Dispersed Active Metal catalysts comprising one or more Group VIII metals.

BACKGROUND OF THE INVENTION

The production of higher hydrocarbon materials from synthesis gas, i.e. carbon monoxide and hydrogen, commonly known as the Fischer-Tropsch process, has been in commercial use for many years. In such processes, the synthesis gas mixture is contacted with a suitable Fischer-Tropsch catalyst under shifting or non-shifting conditions, preferably the latter, wherein little or no water gas shift takes place. Suitable Fischer-Tropsch catalysts comprise one or more Group VIII catalytic metals, such as iron, cobalt and nickel.

There exist many variations of the basic preparation of Fischer-Tropsch catalysts such as, for example, deposition of alloys onto a performed support by flame spraying, (U.S. Pat. No. 4,089,812), formation of the alloy by surface diffusion of aluminum on a non-leachable metal substrate (U.S. Pat. No. 2,583,619), and forming pellets from the powdered alloys for use in fixed bed reaction vessels (U.S. Pat. Nos. 4,826,799, 4,895,994 and 5,536,694, for example). The choice of a particular catalyst formulation, method of fabrication and method of activation depends in large measure on the catalytic activity, the desired product or products, whether or not the catalyst can be regenerated and the specific process components and configurations.

The production of hydrocarbons by the Fisher-Tropsch process may be carried out in virtually any type reactor, e.g. fixed bed, moving bed, fluidized bed, slurry, bubbling bed and the like. A preferred reactor carrying out such reactions is the slurry bubble column developed by Exxon Research & Engineering Company. This reactor, which is ideally suited for carrying out highly exothermic, three-phase catalytic reactions, is described in U.S. Pat. No. 5,348,982. In such reactors, the solid phase catalyst is dispersed or held in suspension in a liquid phase by a gas phase that continuously bubbles through the liquid phase. The catalyst loading in slurry bubble reactors can vary within a broad range of concentrations, but must remain short of the so-termed "mud limit" where the concentration of the catalyst reaches a level such that mixing and pumping of the slurry become so difficult as to render practical operation impossible. The use of high metal-loading catalysts or bulk metal catalysts is preferred in slurry bubble reactors in order to maximize the productivity of both catalyst and reactor.

Particularly suited for the production of hydrocarbons by Fischer-Tropsch synthesis from synthesis gas are Dispersed Active Metals ("DAM") which are primarily, i.e. at least about 50 wt. %, preferably at least 80 wt. %, composed of one or a mixture of metals such as described above and are, without further treatment, capable of catalyzing Fischer-Tropsch synthesis. DAM catalysts may be prepared by any of a number of art-recognized processes. An extensive review of process of forming DAM catalysts can be found in "Active Metals", Edited by Alois Furstner, published by VCH Verlagsgesellschaft mbH, D-69451 Weinheim (FRG) in 1996 and the references cited therein. Methodologies described therein include the Rieke method, the use of ultrasound, reduction of metal salts, colloids, nanoscale cluster and powders. Other relevant references include, for example, the preparation of amorphous iron catalyst by high intensity sonolysis of iron pentacarbonyl, Suslick et al., Nature, Vol. 353, pp 414–416 (1991) and the formation of single domain cobalt clusters by reduction of a cobalt salt with hydrazine, Gibson et el., Science, Vol. 267, pp 1338–1340, (1998). Finally, intermetallic alloys, particularly those known for forming metal hydrides, such as $LaCo_5$, can be formed into a fine powder by the application of hydrogen adsorption/desorption cycles. DAM catalysts can also be prepared by thermal or chemical decomposition of metal formates or oxalates. These methods are given as examples and are not intended in any way to limit the term "DAM" as utilized in the context of the present invention.

There are many well-known methods for the preparation of DAM catalysts in the literature. In 1924, M. Raney prepared a Nickel hydrogenation catalyst by using a process known today as the Raney Process and Raney catalysts. Such catalysts are described and illustrated, for example, in U.S. Pat. No. 4,826,799. The process of preparing these catalysts is, in essence, forming at least a binary alloy of metals, at least one of which can be extracted, and extracting it leaving a porous residue of the non-soluble metal or metals that possesses catalytic activity. These groups of metals are well known to those skilled in the art. The residue catalyst metals include Ni, Co, Cu, Fe and the Group VIII noble metals. The leachable or soluble metal group includes aluminum, zinc, titanium or silicon, typically aluminum. Once the alloys are formed, they are ground to a fine powder and treated to extract the leachable metal, typically with strong caustic, such as sodium hydroxide. Alternatively, the alloy is formed onto or impregnated into a suitable rigid support structure which is then extracted with caustic to form a porous, supported catalyst.

The high metal content of DAM catalysts, i.e. at least 50% metal, represents a major economic impediment to their use unless low cost recovery technology can be implemented as well. Those of ordinary skill in the art are aware that metals constituting DAM catalysts, particularly Raney catalysts, are conventionally recovered by subjecting the used, or spent, catalysts to multiple processing steps, principally for the purpose of purification of the metal. The particular methodology chosen to purify and recover the metal depends in large measure on the nature of the impurities and contaminants that have been deposited on the catalyst during use. In most applications, drastic treatments are required because of significant contamination of the metals by one or more of carbonaceous deposits, heteroorganic compounds, i.e. compounds containing sulfur and/or nitrogen, and other metals.

Typically, spent DAM catalysts are treated in the reactor by oxidation to permit safe unloading and shipping to a metal processing facility. The oxidation can be carried out, for example, by air oxidation of the catalyst slurry, or by treatment with bleach as recommended by catalyst manufacturers. In the metal processing facility, the catalysts are generally roasted in air, dissolved in strong acid and the different metals selectively reprecipitated in the form of salts. The metals may be reused in the form of the salts, or converted back into metallic form, depending on the requirements of the synthesis. Such treatments must be effective and efficient because, although carbon monoxide hydrogenation processes are conducted in an exceptionally clean environment, DAM catalysts are generally sensitive to comparatively minor amounts of contaminants.

Those of ordinary skill in the art recognize that the economic worth of a given catalyst is a function of its original cost, its value as a spent catalyst, e.g. for regeneration of fresh catalyst, its activity and its half-life in the reactor. Another important aspect of the value of a catalyst is its selectivity which is the ratio of the percent of feed material converted to desired higher hydrocarbons to that of short chain hydrocarbons produced, primarily methane, commonly referred to as "methane selectivity". It will be appreciated that a process that will effectively extend the useful life of a catalyst before it must be disposed of through conventional metal recovery will significantly improve the value of that catalyst. Such a process that enhances both the activity and methane selectivity of a catalyst is provided in accordance with the present invention.

SUMMARY OF THE INVENTION

In accordance with the present invention, there is provided a significant improvement in the catalytic hydrogenation of carbon monoxide to form a mixture of hydrocarbons in a reactor wherein the catalyst is a Dispersed Metal Catalyst and is not immobilized comprising, commencing at a point during operation of the reactor to produce said hydrocarbons where performance falls below a predetermined level, withdrawing a mixture of hydrocarbons and a portion of the catalyst and enhancing both the activity and methane selectivity thereof by a process comprising the steps of: reducing the hydrocarbon content of the mixture by heating in a reducing atmosphere, partially oxidizing the DAM particles in a slurry in a suitable fluid at low temperatures to form an oxidized precursor that is subsequently activated by reduction with hydrogen gas at elevated temperature to reform the catalyst which is returned to the reactor.

The hydrocarbon/catalyst mixture may be withdrawn from and replaced into the reactor until performance has risen above a second predetermined level at which point the subject process is halted and the reactor continues to run until performance again falls below a predetermined level, at which point the subject process is recommenced. This cycle will be repeated at least once before continuous operation of the subject process is commenced. Alternatively, once the subject process is commenced, catalyst will be continuously withdrawn from and replaced into the reactor. Once continuous operation of the subject process has begun, the operation of the reactor will be continued until a point is reached where it is evident that economic operation of the reactor cannot be long sustained at which point operation of the reactor can be halted. In a preferred embodiment, instead of halting operation of the reactor, the catalyst is renewed while the reactor continues to run by a process including the formation of a melt as will be described hereinafter. In a further preferred embodiment, catalyst renewed by the process including the formation of a melt is enhanced by treatment according to the process of the invention prior to being returned to the reactor. In a still further embodiment, the renewed, enhanced catalyst particles are passivated as will be described below.

DETAILED DESCRIPTION OF THE INVENTION

Dispersed Active Metals (DAM), which correspond essentially to reduced metals, are utilized in a broad range of applications such as the hydrogenation of fats and specialty chemicals. Start-up procedures, which may include specific activation sequences, are highly dependent upon the catalytic reaction, the process design and, in particular, the reaction vessel design and configuration. The slurry bubble column discussed above is a preferred vessel for carrying out carbon monoxide hydrogenation reactions and also for catalyst enhancement in accordance with the present invention. In such reactors, the solid phase catalyst is dispersed or held in suspension in a liquid hydrocarbon phase by a gas phase, which continuously bubbles through the liquid phase. DAM catalysts useful for such applications have a metallic content of at least 50 wt. %, preferably at least 80 wt. %, in the reduced metallic form. Preferred catalysts include intermetallic alloys or Raney catalysts, for example Raney cobalt. Among the intermetallic alloys, preferred examples are those suitable for forming metal hydrides, such as $LaCo_5$. Most preferably, the DAM catalyst comprises one or more of Co, Ru, Fe and Cu.

Catalysts most suited for use in slurry column reactors vessels typically are in a finely particulate form having an average diameter ranging from 1 to 1,000 lm, preferably from 10 to 500 lm, most preferably from 20 to 100 lm. The use of high metal loading catalysts and/or bulk catalysts is preferred in order to maximize the productivity of the reaction vessel. The present process may be applied to other conventional reaction vessels known in the art wherein the catalyst is not immobilized, such as fluidized bed, slurry, bubbling bed and the like. In such moving bed reactors, contaminated catalyst would typically be withdrawn from the bottom of the vessel and catalyst that had been enhanced in accordance with the present process would be replaced at the top.

In the carbon monoxide hydrogenation reaction, a syngas comprising a mixture of hydrogen and carbon monoxide is bubbled up into the reactive hydrocarbon-containing slurry in which it is catalytically converted into liquid and gaseous products, preferably liquid hydrocarbons, with shifting or non-shifting conditions, preferably the latter, wherein little or no water gas shift takes place. This hydrocarbon synthesis ("HCS") process is generally carried out at temperatures of from about 160° C. to 260° C., pressures of from about 5 atm. to about 100 atm., preferably from 10 atm. to 40 atm., and gas space velocities of from about 300 V/Hr/V to 20,000 V/Hr/V, preferably from about 1,000 V/Hr/V to about 15,000 V/Hr/V. The stoichiometric ratio of hydrogen to carbon monoxide is about 2.1:1 for the production of higher hydrocarbons. This ratio can vary from about 1:1 to 4:1, preferably from 1.5:1 to 2.5:1, more preferably from 1.8:1 to 2.2:1. These reaction conditions are well known to those skilled in the art and a particular set of reaction conditions can readily be determined from the parameters given herein. The hydrocarbon-containing products formed in the process are essentially free of sulfur and nitrogen-containing contaminants.

The hydrocarbons produced in a process as described above are typically upgraded to more valuable products by subjecting all or a portion of the C5+ hydrocarbons to fractionation and/or conversion. By "conversion" is meant one or more operations in which the molecular structure of at least a portion of the hydrocarbon is changed and includes both non-catalytic processing, e.g. steam cracking, and catalytic processing, e.g. catalytic cracking, in which the portion, or fraction, is contacted with a suitable catalyst. If hydrogen is present as a reactant, such process steps are typically referred to as hydroconversion and variously as hydroisomerization, hydrocracking, hydrodewaxing, hydrorefining and the like. More rigorous hydrorefining is typically referred to as hydrotreating. These reactions are conducted under conditions well documented in the literature for the hydroconversion of hydrocarbon feeds, including hydrocarbon feeds rich in paraffins. Illustrative, but non-limiting, examples of more valuable products from such feeds by these processes include synthetic crude oil, liquid fuel, emulsions, purified olefins, solvents, monomers or polymers, lubricant oils, medicinal oils, waxy hydrocarbons, various nitrogen- or oxygen-containing products and the like. Examples of liquid fuels includes gasoline, diesel fuel and jet fuel, while lubricating oil includes automotive oil, jet oil, turbine oil and the like. Industrial oils include well drilling fluids, agricultural oils, heat transfer oils and the like.

Typical Fisher-Tropsch HCS reaction conditions effective to form hydrocarbons comprising mostly C5+ paraffins, (for example C5–C200) and preferably C10+ paraffins in a slurry HCS process employing a catalyst comprising a cobalt component include, for example, temperatures, pressures and gas hourly space velocities in the range of from about 160–260° C., 5–40 atm. and 100–40,000 V/hr/V, expressed as standard volumes of the gaseous carbon monoxide and hydrogen mixtures (25° C., 1 atm.) per hour per volume of catalyst, respectively. The syngas utilized in carbon monoxide hydrogenation may be formed by various means known to those of ordinary skill in the art, such as a fluid bed syngas-generating unit as is disclosed, for example, in U.S. Pat. Nos. 4,888,131, and 5,160,456. Regardless of the source, syngas typically contains chemical species, such as ammonia and hydrogen cyanide, which will, over time, cause deactivation of the catalyst. Other deactivating chemical species may be formed during the carbon monoxide hydrogenation process. Those skilled in the art are aware of the fact that deactivation by those contaminants is generally reversible and the catalyst can be rejuvenated by treatment with hydrogen. However, catalyst deactivation that cannot be rejuvenated is caused by the formation of refractory carbonaceous residues and/or permanent poisons such as sulfur, phosphorus, halides and other metal contaminants.

A decrease in reactor performance or increase in operational problems may also be caused by the formation of fines resulting from the disintegration of catalyst particles due to the turbulent environment in the reactor. While the criteria for what are considered fines particles may vary with the reactor, typically fines have a particle size of less than 10 microns. Fines can cause clogging within the reactor and are as much of an inactivating factor over time as are permanent poisons. The present process is concerned with contamination that is generally reversible.

In accordance with the present invention, both the activity and selectivity, i.e. methane selectivity, of the DAM catalyst utilized in the HCS process are enhanced during operation of the reactor. The process is commenced by the withdrawal from the reactor of a mixture of hydrocarbon, typically molten wax, and a portion of the catalyst. While it is intended that all or substantially all of the catalyst in the reactor be treated in accordance with the process of the invention, those of ordinary skill in the art will appreciate that it is necessary that sufficient catalyst remain in the reactor to sustain the desired level of production. Although the amount of catalyst removed can vary within a wide range, typically from about 0.01 wt. % to about 10 wt. % of the catalyst will be removed from the reactor at a given point in time during production. It is not intended that such amount of catalyst be removed in a single quantity. Rather, portions of the withdrawn catalyst will be at various stages of the process of the invention at any given time so that, when a portion is returned to the reactor, an estimated like amount can be withdrawn.

The hydrocarbon content of the mixture withdrawn from the reactor is essentially similar to that of the reactor at the mixture collection port. Those skilled in the art will recognize that the hydrocarbon content of the mixture depends upon the type of reactor utilized and it's operating conditions. For example, it is expected that a lower hydrocarbon content will be obtained when operating a bubble column reactor with a slumped bed as opposed to operating it with a conventional dispersed bed reactor.

The catalyst-hydrocarbon mixture withdrawn from the reactor is initially treated to reduce its hydrocarbon content. This is carried out by contacting the mixture with a hydrogen-containing gas at a temperature at least 20° C., preferably at least 50° C., higher than that of the reactor. It is preferred that the mixture be contacted with the hydrogen-containing gas, even if an alternative methodology is initially utilized to reduce the hydrocarbon content thereof. Such alternative methodologies include, for example, gravitational or centrifugal separation which allows the hydrocarbon to be decanted or removed by filtration, or treatment with a solvent or supercritical fluid that effectively weakens the interaction of the hydrocarbon with the catalyst surface so that the liquid and solid phases can readily be separated in the same manner. Suitable solvents include, for example, paraffin solvents or naphthas, alcohols, and aromatic solvents. Supercritical fluids include, for example, carbon dioxide, light paraffins and cyclopropane. The mixture may also be contacted with an oxygen-containing gas or steam at elevated temperature to effectively reduce the hydrocarbon content.

While it is contemplated to utilize any of these alternate methods of reducing the hydrocarbon content of the mixture withdrawn from the reactor as a first step preceding the hydrogen treatment, typically the physical separations such as decanting or centrifugation are preferred since the mixture withdrawn from the reactor generally contains both solid and liquid phases. For example, for a mixture containing from 1 to 50%, typically from 2 to 40%, of wax, physical separation, i.e. centrifugation/decanting or filtration to remove liquid hydrocarbons may advantageously be combined with subsequent treatment with hydrogen-containing gas at elevated temperature to separate, then dewax, the catalyst particles. Typically, the hydrogen pressure would be from atmospheric to about 1000 psi, preferably from 10 to 400 psi. The duration of the hydrocarbon lowering, or dewaxing, is adjusted to produce a residual carbon content of less than 5 wt. %, preferably less than 2 wt. %.

In accordance with the present invention, the reduced hydrocarbon mixture formed as described above is treated by slurry low temperature oxidation as described in copending patent application, the disclosure of which is incorporated herein by reference. In this treatment, a slurry of the reduced hydrocarbon mixture in a suitable fluid is incompletely oxidized at low temperature to form an oxidized catalyst precursor that is a mixture of metallic and oxidic species, i.e. oxides and, wherein the fluid is or contains water, hydroxides. The oxidant utilized in this step may be either a gaseous oxidant or a solution of a soluble, non-gaseous oxidant in a suitable solvent. Suitable solvents are miscible with the fluid utilized to from the slurry or, preferably, the fluid itself. By low temperature is meant a temperature below 200° C., preferably below 100° C. Typical oxidative gases include oxygen, ozone and nitrogen oxides, i.e. nitrous oxide and nitric oxide, and suitable gas mixtures containing them. Soluble oxidants utilized in solution may include, without intended limitation, nitric acid, an inorganic nitrate, for example ammonium nitrate, hydrogen peroxide or art-recognized organic peroxides or hydroperoxides.

Preferred fluids for slurry low temperature oxidation include, for example, water, mixtures of water and organic solvents, hydrocarbons, particularly those derived from the Fischer-Tropsch synthesis itself, or supercritical fluids such as carbon dioxide, liquid phase light hydrocarbons, i.e. C3–5 alkanes, cyclopentane and the like. Preferred mixed liquids include, without any intended limitation, mixtures or emulsions of water, hydrocarbons and lower alkanols. A preferred fluid is the liquid hydrocarbon mixture separated from the catalyst particles as described above. After this treatment, the oxidized catalyst precursor particles may be recovered by physical separation, i.e. gravitational or centrifugal separation, followed by filtration.

The oxidized catalyst precursor particles are treated to reform the active catalyst by reduction with hydrogen-containing gas at elevated temperatures, i.e. from about 200° C. to 600° C., preferably from about 300° C. to 450° C., most preferably from about 340° C. to 400° C. Hydrogen partial pressure during the reduction would range from about 1 to 100 atmospheres, preferably from about 1 to 40 atmospheres. The active DAM catalyst particles treated in accordance with the present invention, whose activity is substantially enhanced, are then returned to the reactor. This may be carried out by forming a slurry of the DAM particles in liquid hydrocarbon, conveniently the hydrocarbon mixture withdrawn from the reactor to initiate the process from which the catalyst has been separated, or by suspending the particles in a non-oxidizing gas, preferably a reducing gas, or by gravity or pressure gradient, or any combination thereof.

It is within the scope of the present invention to passivate the enhanced catalyst particles before returning them to the hydrocarbon synthesis reactor. The passivation may be carried out by contacting the catalyst particles with a gas containing carbon monoxide, or carbon monoxide and hydrogen, under conditions such that carbon monoxide does not significantly decompose and is not significantly hydrogenated. Such conditions, for example, would be a temperature below about 150° C., preferably between about 25° C. and 100° C., and pressure below about 20 atm., particularly between about 1 and 10 atm. Those of ordinary skill in the art will appreciate that some decomposition or hydrogenation, respectively, of the carbon monoxide may take place regardless of the precautions taken by the operator. Hence, by "significantly" is meant that such decomposition/hydrogenation does not exceed 5% by volume of the feed gas. It has been found that catalysts that have been passivated in this manner typically exhibit higher initial carbon monoxide hydrogenation activity than similar, but unpassivated, catalysts. Other passivating agents include, for example, traces of oxygen or carbon dioxide.

The process of the present invention will be commenced at a point in time when the performance of a reactor that has been started with fresh catalyst declines to a predetermined level. While the point at which the process of the present invention is initiated may vary with a number of factors, it should be a level of performance where the reactor is still operating in an efficient manner, but performance has significantly declined. As stated previously, performance is primarily measured by two criteria, catalyst activity and methane selectivity. While the determining point is relatively arbitrary and is influenced by the process itself, the configuration of the reactor, the economies of the reactor and the like, a level should be chosen that will enable the process of the invention to enhance the performance of the catalyst before it declines to where performance becomes unacceptable. For purposes of illustration, the process of the present invention will be initiated when either aspect of the performance of the catalyst has declined to about 60% of its original level.

When the process of the invention is initiated and catalyst withdrawal has begun, the process may be run continuously to a point where the reactor must be stopped due to its performance reaching a level such that it can no longer be economically operated. It will be appreciated that the same considerations will apply to the determination of such an end point as were utilized in determining when to initiate the process of the invention. Alternatively, the process of the present invention is continued until it is determined that substantially all of the catalyst originally present in the reactor has been enhanced. Given the amount of catalyst present in the reactor and the rate of withdrawal, the determination of when substantially all of the catalyst has been enhanced by the present method is considered to be within the level of skill of the art. Enhancing substantially all of the catalyst will substantially restore the original activity of the catalyst. When the enhancement is completed, the process of the invention is discontinued and the reactor again operated until performance reaches a second predetermined level.

The process of the present invention will substantially enhance the activity of the DAM catalyst particles. It will be appreciated by those of ordinary skill in the art that, over time, as the reactor continues to operate, the activity of the withdrawn particles is decreased as, for example, a result of the buildup of permanent poisons and fines as described above. As the reactor continues to operate, a second predetermined point will be reached where the performance has again declined to a level such that the process of the present invention must again be initiated. This second point may be a performance level at or below that where the process was first initiated. If the same point is utilized, it will be appreciated that it may be reached in less time than passed before the process was first initiated. When it is calculated that substantially all of the catalyst in the reactor has been treated in accordance with the subject process, it may again be discontinued and the reactor operated for another period of time as described above until a further predetermined level of performance is reached.

Two or more cycles of operating with and without the process of the invention as described are contemplated before operation of the process of the invention should become continuous. Again, the number of cycles is within the purview of the skilled operator. Generally, the skilled operator will observe that, over time, operating the reactor without the process of the invention does not present an appreciable advantage over continuous operation in terms of the advantage to be gained in contrast to the manipulative steps that must be carried out. Therefore, regardless of whether continuous operation of the process of the invention follows initial inception or at least two cycles as described above, a point will be reached where, in spite of the operation of the process of the invention, it will become evident to the skilled operator that operation cannot continue for en extended period of time before it becomes uneconomical to do so. This may be the result of the build-up of permanent poisons and/or fines. There are a number of factors that determine the level of economic advantage, or practicality of a reactor continuing to operate under a given set of conditions. These include the configuration of the reactor, the process being run, the value of both the catalyst and the product, the selectivity of the reaction, and the like.

At a point where it is evident to the skilled operator that the reactor can no longer be operated to economic advantage, the operation of both the process of the present invention and the reactor may be shut down as noted above and the catalyst withdrawn and returned to the manufacturer for regeneration. In a preferred embodiment of the present invention, the catalyst is withdrawn by portions while the reactor continues to operate, and treated to renew it. It will be appreciated that sufficient time must be allowed to permit return of the renewed catalyst to begin since that will exert a positive effect on the overall operation of the reactor.

The process of renewing the catalyst, which is disclosed and claimed in copending patent application, comprises treating a mixture of catalyst and hydrocarbon withdrawn from the reactor to reduce the hydrocarbon content thereof, heating the resulting mixture under a non-oxidizing atmosphere to a temperature above the melting temperature of at least one of the metals present in the catalyst thereby forming a melt, removing any impurities slag that forms on the melt, cooling the melt to solidify it, treating the resultant solid to reduce the particle size thereof to a fine powder of renewed catalyst and returning it to the reactor.

Wherein the catalyst is a DAM catalyst, the process of treating the solid formed upon cooling the melt to form fine particles of renewed catalyst is carried out by a series of hydrogen absorption/desorption cycles which performs both functions, i.e. reducing the particle size and renewal of catalyst activity. Wherein the catalyst is a non-supported Raney catalyst, a leachable metal is added to the reduced hydrocarbon mixture or the melt, the solid formed upon cooling is reduced to a fine particle size and the metal leached or dissolved from the particles with a suitable solvent therefor. Preferred leachable metals are aluminum, titanium, silicon and zinc, and the preferred solvent is caustic.

This renewal process may be commenced while the process as described above continues to operate, may be run on only fines separated from the withdrawn mixture while the remaining particles are subjected to the process of the present invention, or may be followed by the process of the present invention to further enhance the renewed catalyst particles before they are returned to the reactor. A still further enhancement of the catalyst prior to returning it is to passivate it in the same manner as has been described above. In this manner, it is possible to operate a reactor for extended periods of time before it would have to be shut down for normal maintenance and the like, a considerable economic advantage.

It is understood that various other embodiments and modifications in the practice of the invention will be apparent to, and can be readily made by, those of ordinary skill in the art without departing form the scope and spirit of the invention as described above. For example, although the process has been described in terms of being integrated into a Fischer-Tropsch synthesis to rejuvenate and return DAM catalyst particles during operation of a reactor, the process can be utilized as a stand-alone operation as well. Accordingly, it is not intended that the scope of the claims appended hereto be limited to the exact description set forth above, but rather that the claims be construed as encompassing all of the features of patentable novelty that reside in the present invention, including all the features and embodiments that would be treated as equivalents thereof by those skilled in the art to which the invention pertains. The invention is further described with reference to the following experimental work.

EXAMPLE 1

Treatment of Cobalt Catalyst by Slurry Low Temperature Oxidation

A slurry of about 1200 grams of commercial catalyst (Raney® 2700) in water was placed in a 4 liter beaker and stirred with a Teflon®-coated stirring blade. A total of 1320 cc of 0.5N nitric acid solution was added to the slurry by slow addition. During the addition, the temperature of the slurry rose to about 60° C. and a strong ammonia odor developed. The slurry was stirred for an additional hour following completion of the addition. During the oxidation of the catalyst, the pH of the slurry became basic due to the reduction of the nitrate ions to ammonium ions. The total amount of nitrate ions added was adjusted in order to achieve a complete consumption of the hydrogen dissolved in the catalyst and the native hydrogen generated by the acidic oxidation of the metal in the catalyst. Further addition of nitric acid would result in a dissolution of cobalt ions into the solution, evidenced by a pink coloration, which is undesirable. The deactivated catalyst was filtered, washed three times with deionized water recovered by filtration. During the filtration, the solids were again washed three times with deionized water. The solids were dried overnight in a vacuum oven at 60° C. The catalyst was further treated in flowing air at 120° C. to complete passivation. The passivated catalyst was stored as is without additional storage precautions, yield 946.6 grams of dried, enhanced Raney cobalt catalyst.

EXAMPLE 2

Testing of Enhanced Catalyst

The enhanced catalyst prepared in Example 1 was tested in a laboratory fixed bed reactor. A sample (1 cc, 2.32 g) of the catalyst was mixed with quartz diluent (5 cc, 8.18 g) and placed into a 1 cm inside diameter tubular reactor. The catalyst bed was held in place with a plug of glass wool at the bottom of the bed.

A multipoint thermocouple was inserted into the bed to monitor temperatures The Catalyst was reduced with hydrogen at 375° C., 280psig and 315 sccm for two hours. The catalyst was cooled to 177° C., 280 g under a flow of 10 sccm argon and 260 sccm hydrogen. After cooling, the feed was changed to 12 sccm argon, 134 sccm hydrogen and 94 sccm of a blend of CO and CO2, giving a nominal feed composition of 56.3% hydrogen, 11.3% carbon dioxide, 5.5% argon, and 26.9% carbon monoxide where the percentages are given as mole percent. The reactor was then gradually and uniformly heated to 200° C. over a period of eight hours and maintained at that temperature for an additional 24 hours. The reactor was then again gradually and uniformly heated to 213° C. over a period of five hours. During this time and for the remainder of the test the pressure was kept constant at 280 psig. After reaching 213° C., the catalyst demonstrated a CO conversion of 55.0% and a methane selectivity of 7.5%. Methane selectivity is the carbon in the produced methane as a percentage of the total in the converted CO. After three days under these conditions, the CO Conversion was 48.5% and the methane selectivity was 7.7%.

EXAMPLE 3

Preparation of Severely Deactivated Catalyst

In this Example, the use of a catalyst under conditions of poor heat management results in excessive temperatures causing hot spots in the catalyst bed and rapid loss of catalyst activity and selectivity. The condition of poor heat management was established by using a low ratio of diluent to catalyst. In contrast to Example where the ratio of catalyst to diluent was approximately 1:5, the ratio herein was approximately 1:1, utilizing 3 cc, 6.96 g of catalyst and 3 cc, 4.79 g of quartz diluent. All other conditions as described in Example 2 were carried out. After the point in Example 2 where the reactor was slowly heated until the temperature reached 213° C. at a constant pressure of 280 psig, the catalyst demonstrated a CO conversion of 55.9% and a methane selectivity of 34.1%. After 4.1 days under these conditions, the CO conversion was 31.5% and the methane selectivity was 34.1%. The feed was changed to 315 sccm of hydrogen and the reactor heated at the rate of approximately 38° C. to a temperature of 260° C. while maintaining the pressure at 280 psig. These conditions of temperature, hydrogen flow and pressure were maintained for three hours after which the hydrogen flow was stopped and the reactor allowed to cool. The catalyst was discharged from the reactor and the catalyst separated from the diluent with a magnet, all under a nitrogen atmosphere.

EXAMPLE 4

Testing of Severely Deactivated Catalyst

The severely deactivated catalyst prepared in Example 3 was tested in a laboratory fixed bed reactor. A sample (1 cc, 2.32 g) of the catalyst was mixed with quartz diluent (5 cc, 8.18 g) and placed into a 1 cm inside diameter tubular reactor. The catalyst bed was held in place with a plug of glass wool at the bottom of the bed. Both the mixing and reactor loading were carried out under a nitrogen atmosphere in order to prevent undesirable oxidation of the hydrogen dewaxed catalyst. A multipoint thermocouple was inserted into the bed to monitor temperatures. The catalyst was reduced with hydrogen at 375° C., 280 psig and 315 sccm for two hours. The catalyst was cooled to 177° C., 280 psig under a flow of 10 sccm argon and 260 sccm hydrogen. After cooling, the feed was changed to 12 sccm argon, 134 sccm hydrogen and 94 sccm of a blend of CO and CO2, giving a nominal feed composition of 56.3% hydrogen, 11.3% carbon dioxide, 5.5% argon, and 26.9% carbon monoxide where the percentages are given as mole percent. The reactor was then gradually and uniformly heated to 200° C. over a period of eight hours and maintained at that temperature for an additional 24 hours. The reactor was then again gradually and uniformly heated to 213° C. over a period of five hours. During this time and for the remainder of the test the pressure was kept constant at 280 psig. After reaching 213° C., the catalyst demonstrated a CO conversion of 19.1% and a methane selectivity of 27.7%. After 1.4 days under these conditions, the CO conversion was 18.5% and the methane selectivity was 25.7%. This Example demonstrated that the decline in performance if the severely deactivated catalyst produced in Example 3 was relatively permanent and not merely a function of the operating conditions.

EXAMPLE 5

SLTO treatment of Severely Deactivated Catalyst

All steps being conducted under nitrogen, an aliquot of 2.32 g of the severely deactivated catalyst from Example 3 was mixed with 2 cc of deionized water and 1 cc of 0.5N nitric acid was added thereto. The mixture was mixed by shaking for ten minutes after which it was allowed to remain in the vessel for another 30 minutes. The sample was filtered, washed three times with deionized water and then dried in a vacuum over at 80° C. for three hours. The sample could be stored as is without conventional precautions such as the use of an inert atmosphere.

EXAMPLE 6

Testing of SLTO-treated Severely Deactivated Catalyst

The SLTO-treated severely deactivated catalyst prepared in Example 5 was tested in a laboratory fixed bed reactor. A sample (1 cc, 2.32 g) of the catalyst was mixed with quartz diluent (5 cc, 8.18 g) and placed into a 1 cm inside diameter tubular reactor. The catalyst bed was held in place with a plug of glass wool at the bottom of the bed. A multipoint thermocouple was inserted into the bed to monitor temperatures. The catalyst was reduced with hydrogen at 375° C., 280 psig and 315 sccm for two hours. The catalyst was cooled to 177° C., 280 psig under a flow of 10 sccm argon and 260 sccm hydrogen. After cooling, the feed was changed to 12 sccm argon, 134 sccm hydrogen and 94 sccm of a blend of CO and CO2, giving a nominal feed composition of 56.3% hydrogen, 11.3% carbon dioxide, 5.5% argon, and 26.9% carbon monoxide where the percentages are given as mole percent. The reactor was then gradually and uniformly heated to 200° C. over a period of eight hours and maintained at that temperature for an additional 24 hours. The reactor was then again gradually and uniformly heated to 213° C. over a period of five hours. During this time and for the remainder of the test the pressure was kept constant at 280 psig. After reaching 213° C., the catalyst demonstrated a CO conversion of 58.4% and a methane selectivity of 7.2%. After three days under these conditions, the CO conversion was 49.3% and the methane selectivity was 7.5%.

This Example clearly demonstrates the capacity of the process of the invention to enhance and restore the activity of even a severely deactivated catalyst. The results can be readily appreciated from the following Table.

TABLE

| | Catalyst | | |
| --- | --- | --- | --- |
| Example No. | Fresh SLTO Treated 2 | Severely Deactivated 4 | SLTO-treated Deactivated 6 |
| Initial Performance At 213° C. | | | |
| CO Conversion, % | 55.0 | 19.1 | 58.4 |
| CH$_4$ Selectivity, % | 7.5 | 27.7 | 7.2 |
| Performance After Indicated Number Of Days At 213° C. | 3.0 | 1.4 | 3.0 |
| CO Conversion, % | 48.5 | 18.5 | 49.3 |
| CH$_4$ Selectivity, % | 7.7 | 25.7 | 7.5 |

It is also evident from the results shown in the Table that the stability of the severely deactivated catalyst treated by slurry low temperature oxidation in accordance with the method of the invention is comparable to similarly treated fresh catalyst.

What is claimed is:

1. A process for the catalytic hydrogenation of carbon monoxide to form a mixture or hydrocarbons in a reactor utilizing a particulate Dispersed Active Metal Catalyst (DAM) that is not immobilized, said catalyst comprising one or more members selected from the group consisting of Group VIII metals and copper, said process including enhancing the catalyst during operation of the reactor to produce said hydrocarbons by the following steps:
    a) withdrawing a mixture comprising hydrocarbons and a portion of said catalyst particles from the reactor;
    b) contacting the mixture with a hydrogen-containing gas at a temperature above the temperature in the reactor to reduce the hydrocarbon content thereof;
    c) forming a slurry of the catalyst particles in a suitable liquid;
    d) contacting the catalyst with an oxidizing agent at temperatures below about 200° C. thereby forming a partially oxidized catalyst precursor comprising metals and at least one of hydroxides thereof and oxides thereof;

e) reducing said oxidized catalyst precursor with a hydrogen-containing gas at a temperature from about 200° C. to about 600° C. thereby reforming the catalyst; and f) returning the catalyst to the reactor.

2. A process in accordance with claim 1, wherein, in step b) the mixture withdrawn from the reactor is treated to remove liquid hydrocarbons therefrom prior to said treatment with hydrogen-containing gas by one or more of the following steps:

gravitational or centrifugal separation of the catalyst particles from the liquid hydrocarbons and decanting the liquid hydrocarbons therefrom;

filtration of the mixture; and treatment of the mixture with a solvent or supercritical fluid that weakens the interaction between the particles and the hydrocarbons, followed by separation of the resultant liquid and solid phases.

3. A process in accordance with claim 1, wherein, in step b) the mixture withdrawn from the reactor is heated with a hydrogen-containing gas at a temperature of at least about 20° C. higher than that in the reactor.

4. A process in accordance with claim 1, wherein oxidizing agent utilized in step d) is a gaseous oxidant selected from the group consisting of oxygen, ozone, nitrogen oxides and gas mixtures containing them.

5. A process in accordance with claim 1, wherein oxidizing agent utilized in step d) is a soluble oxidant selected from the group consisting of nitric acid, an inorganic nitrate, hydrogen peroxide, organic peroxides and hydroperoxides.

6. A process in accordance with claim 1, wherein the catalyst is reformed in step e) by reducing said oxidized catalyst precursor with a hydrogen-containing gas at a temperature from about 300° C. to about 450° C.

7. A process in accordance with claim 1, wherein in step f), the catalyst is returned to the reactor by one or more of:

forming a slurry of the catalyst with liquid hydrocarbons and introducing said slurry into the reactor;

forming a suspension of the catalyst in a non-oxidizing gas and introducing said suspension into the reactor; or transferring the catalyst to the reactor by gravity or pressure gradient.

8. A process in accordance with claim 1, wherein prior to being returned to the reactor, the catalyst is passivated by:

treatment with a carbon monoxide-containing gas under conditions such that the carbon monoxide is not significantly decomposed; or treatment with a gas containing carbon monoxide and hydrogen under conditions such that the carbon monoxide is not significantly hydrogenated.

9. A process in accordance with claim 1, wherein the process is initiated when the performance of fresh catalyst in the reactor has reached a predetermined level, carried out until substantially all of the catalyst in the reactor has been treated, discontinued, subsequently recommenced when the performance of the catalyst has reached a predetermined level and thereafter operated continuously, wherein said steps of discontinuing and recommencing the process when a predetermined level of performance has been reached are carried out at least once.

10. A process in accordance with claim 1, wherein the process is initiated when the performance of fresh catalyst has reached a predetermined level and thereafter operated continuously during operation of the reactor.

11. A process in accordance with claims 9 or 10, wherein the process is operated to a point in time whereat it is evident that the build-up of at least one of permanent poisons and fines has reached a level such that continued operation of the reactor will become impractical at which time operation of the reactor is stopped.

12. A process in accordance with claim 11 wherein, at said point, and while the reactor continues to operate, a mixture of hydrocarbons and a portion of the catalyst is withdrawn from the reactor and renewed by:

treating said mixture to reduce the hydrocarbon content thereof;

heating the resulting mixture in a non-oxidizing atmosphere to a temperature above the melting temperature of at least one of said metals thereby substantially removing non-metallic impurities therefrom and forming a slag of any refractory metal oxides therein on the resulting melt;

removing the slag, if present;

cooling the melt to solidify it;

treating the solid to reduce the particle size thereof to a fine powder of renewed catalyst; and returning the catalyst to the reactor.

13. A process in accordance with claim 12, wherein the catalyst is further treated by a repetition of steps c) through e) before being returned to the reactor.

14. A process in accordance with claim 13, wherein prior to being returned to the reactor, the catalyst is passivated by:

treatment with a carbon monoxide-containing gas under conditions such that the carbon monoxide is not significantly decomposed; or treatment with a gas containing carbon monoxide and hydrogen under conditions such that the carbon monoxide is not significantly hydrogenated.

15. An enhanced particulate Dispersed Active Metal (DAM) catalyst formed during the production of a mixture of hydrocarbons by catalytic hydrogenation of carbon monoxide in a reactor wherein the catalyst is not immobilized, said catalyst comprising one or more members selected from the group consisting of Group VIII metals and copper, said catalyst being formed by:

a) withdrawing a mixture comprising hydrocarbons and a portion of said catalyst particles from the reactor;

b) contacting the mixture with a hydrogen-containing gas at a temperature above the temperature in the reactor to reduce the hydrocarbon content thereof;

c) forming a slurry of the catalyst particles in a suitable liquid;

d) contacting the catalyst with an oxidizing agent at temperatures below above 200° C. thereby forming an oxidized catalyst precursor comprising metals and at least one of hydroxides thereof and oxides thereof; and e) reducing said oxidized catalyst precursor with a hydrogen-containing gas at a temperature from about 200° C. to about 600° C. thereby reforming the catalyst.

16. A catalyst in accordance with claim 15 comprising a plurality of metals, wherein one of said metals is cobalt.

17. A process for producing higher hydrocarbons by the hydrogenation of carbon monoxide by reaction with hydrogen at reaction conditions in the presence of a renewed catalyst according to claim 15.

18. A process in accordance with claim 17, wherein at least a portion of the hydrocarbons formed are upgraded to more valuable products by at least one of fractionation and conversion operations.

19. A process in accordance with claim 16, wherein said metals comprise cobalt, or cobalt and a minor quantity of a metal that is a promoter for the catalytic activity thereof in the hydrogenation process.

\* \* \* \* \*